(12) United States Patent
Bennett et al.

(10) Patent No.: US 9,856,499 B2
(45) Date of Patent: Jan. 2, 2018

(54) LONG CHAIN ORGANIC ACID BIOPRODUCTION

(71) Applicant: William Marsh Rice University, Houston, TX (US)

(72) Inventors: George N. Bennett, Houston, TX (US); Xianpeng Cai, Houston, TX (US)

(73) Assignee: William Marsh Rice University, Houston, TX (US)

( * ) Notice: Subject to any disclaimer, the term of this patent is extended or adjusted under 35 U.S.C. 154(b) by 56 days.

(21) Appl. No.: 14/355,402

(22) PCT Filed: Dec. 20, 2012

(86) PCT No.: PCT/US2012/071038
§ 371 (c)(1),
(2) Date: Apr. 30, 2014

(87) PCT Pub. No.: WO2013/096665
PCT Pub. Date: Jun. 27, 2013

(65) Prior Publication Data
US 2015/0044743 A1 Feb. 12, 2015

Related U.S. Application Data

(60) Provisional application No. 61/579,480, filed on Dec. 22, 2011.

(51) Int. Cl.
| | | |
|---|---|---|
| C12P 7/52 | (2006.01) | |
| C12N 1/20 | (2006.01) | |
| C12N 1/38 | (2006.01) | |
| C12P 7/40 | (2006.01) | |

(52) U.S. Cl.
CPC .............. *C12P 7/52* (2013.01); *C12N 1/20* (2013.01); *C12N 1/38* (2013.01); *C12P 7/40* (2013.01)

(58) Field of Classification Search
None
See application file for complete search history.

(56) References Cited

U.S. PATENT DOCUMENTS

| | | |
|---|---|---|
| 2009/0215163 A1 | 8/2009 | Tsai et al. |
| 2010/0028966 A1 | 2/2010 | Blanchard et al. |
| 2014/0093921 A1 | 4/2014 | San |
| 2014/0193867 A1 | 7/2014 | San |
| 2014/0212935 A1 | 7/2014 | San |

OTHER PUBLICATIONS

Kim et al. "Redox Potential in Acetone-Butanol Fermentations". Applied Biochemistry and Biotechnology. 1988, 18(1): 175-186.*
Peguin et al. "Modulation of metabolism of Clostridium acetobutylicum growth in chemostat culture in three-electrode potentiostatic system with methyl viologen as electron carrier". Biotechnology and Bioengineering. 1996, vol. 51, pp. 342-348.*
Price-Whelan et al. Journal of Bacteriology. 2007, vol. 189, No. 17, pp. 6372-6381.*
Stankovich et al. Biochemica and Biophysica Acta. 1976, vol. 452, pp. 335-344.*
Information at webpage "Traditional Oven", http://www.tradionalovaen.com//foods/specific-nutrinet/yeast-extract-spead/riboflvain-b2-vitamin.html; retrieved on Dec. 6, 2016.*
Padda, R. S., Wang, C. Y., Hughes, J, R., and Bennett, G. N. (2000) Mutagenicity of trinitrotoluene and its metabolites formed during anaerobic degradation by Clostridium acetobutylicum ATCC 824. Environ. Toxicol. Chem. 19, 2871-2875.
Padda, R. S., Wang, C Y., Hughes, J. B., Kutty, R.and Bennett, G. N. (2003) Mutagenicity of nitroaromatic degradatino compounds. Environ. Toxicol. Chem. 22, 2293-2297.
Peguin, S., and Soucaille, P. (1995) Modulation of Carbon and Electron Flow in Clostridium acetobutylicum by Iron Limitation and Methyl Viologen Addition. Applied and environmental microbiology 61, 403-405.
Kutty, R., and Bennett, G. N. (2006) Studies on inhibition of transformation of 2,4,6-trinitrotoluene catalyzed by Fe-only hydrogenase from Clostridium acetobutylicum. J Ind Microbiol Biotechnol 33, 368-376.
Aristidou, A. A., San, K. Y., and Bennett, G. N. (1999) Improvement of biomass yield and recombinant gene expression in *Escherichia coli* by using fructose as the primary carbon source. Biotechnology progress 15, 140-145.
Daun, G., Lenke, H., Reuss, M., and Knackmuss, H. J. (1998) Biological treatment of TNT-contaminated soil. 1. Anaerobic cometabolic reduction and interaction of TNT and metabolites with soil components. Environ. Sci. Technol. 32, 1956-1963.
Frische, T., and Hoper, H. (2003) Soil microbial parameters and luminescent bacteria assays as indicators for in situ bioremediation of TNT-contaminated soils. Chemosphere 50, 415-427.
Wu, Y., Luo, Y., Zou, D., Ni, J., Liu, W., Teng, Y., and Li, Z. (2008) Bioremediation of polycyclic aromatic hydrocarbons contaminated soil with *Monilinia* sp.: degradation and microbial community analysis. Biodegradation 19, 247-257.
King, P.W., et al., (2006) Functional Studies of [FeFe] Hydrogenase Maturation in an *Escherichia coli* Biosynthetic System, J. Bacteriol. 188(6), 2163-2172.
Cai, X., and Bennett, G. N. (2011) Improving the Clostridium acetobutylicum butanol fermentation by engineering the strain for co-production of riboflavin. Journal of industrial microbiology & biotechnology 38, 1013-1025.
Eyers, L., Smoot, J. C., Smoot, I. M., Bugli, C., Urakawa, H., McMurry, Z., Siripong, S., El-Fantroussi, S., Lambert, P., Agathos, S. N., and Stahl, D. A. (2006) Discrimination of shifts in a soil microbial community associated with TNT-contamination using a functional ANOVA of 16S rRNA hybridized to oligonucleotide microarrays. Environmental science & technology 40, 5867-5873.
Zhao, Y., Hindorff, L. A., Chuang, A., Monroe-Augustus, M., Lyristis, M., Harrison, M. L., Rudolph, F. B., and Bennett, G. N. (2003) Expression of a cloned cyclopropane fatty acid synthase gene reduces solvent formation in Clostridium acetobutylicum ATCC 824. Appl Environ Microbiol 69, 2831-2841.

(Continued)

*Primary Examiner* — Vera Afremova
(74) *Attorney, Agent, or Firm* — Boulware & Valoir

(57) ABSTRACT

Method of cell culture, comprising adding a redox active compound with a redox potential of between −0.116 to −0.253 to a culture capable of forming hydrogen via a hydrogenase so that the redox potential is diverted from hydrogen to form a longer chain acids, e.g., butryic acid.

3 Claims, 6 Drawing Sheets

(56) References Cited

OTHER PUBLICATIONS

Figure 1:
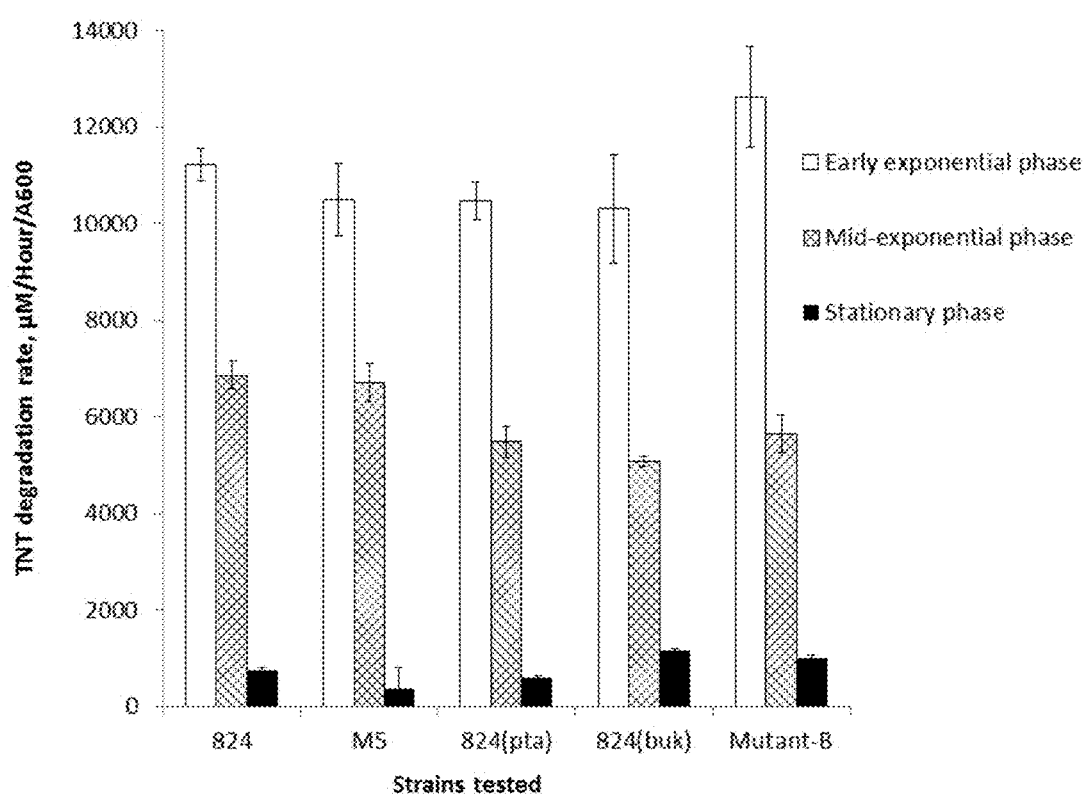

Girbal, L., and Soucaille, P. (1994) Regulation of Clostridium acetobutylicum metabolism as revealed by mixed-substrate steady-state continuous cultures: role of NADH/NAD ratio and ATP pool. J Bacteriol 176, 6433-6438.

Watrous, M. M., Clark, S., Kutty, R., Huang, S., Rudolph, F. B., Hughes, J. B., and Bennett, G. N. (2003) 2,4,6-trinitrotoluene reduction by an Fe-only hydrogenase in Clostridium acetobutylicum. Appl Environ Microbiol 69, 1542-1547.

Zhao, Y., Tomas, C. A., Rudolph, F. B., Papoutsakis, E. T., and Bennett, G. N. (2005) Intracellular butyryl phosphate and acetyl phosphate concentrations in Clostridium acetobutylicum and their implications for solvent formation. Appl Environ Microbiol 71, 530-537.

Won, W. D., Salvo, L. H. d., and NG, J. (1976) Toxicity and mutagenicity of 2,4,6-trinitrotoluene and its microbial metabolites. Appl. Environ Microbiol. 31, 576-580.

Van Der Zee, F. P., Bouwman, R. H., Strik, D P., Lettinga, G., and Field, J. A (2001) Application of redox mediators to accelerate the transformation of reactive azo dyes in anaerobic bioreactors. Biotechnology and bioengineering 75, 691-701.

Tan, E. L., Ho, C. H., Griest, W. H., and Tyndall, R. L. (1992) Mutagenicity of trinitrotoluene and its metabolites formed during composting. J. Toxicol. Environ. Health 36, 165-172.

Vasconcelos, I., Girbal, L., and Soucaille, P. (1994) Regulation of carbon and electron flow in Clostridium acetobutylicum grown in chemostat culture at neutral pH on mixtures of glucose and glycerol. J Bacterial 176, 1443-1450.

Siciliano, S. D., Gong, P., Sunahara, G. I., and Greer, C. W. (2000) Assessment of 2,4,6-trinitrotoluene toxicity in field soils by pollution-induced community tolerance, denaturing gel electrophoresis, and seed germination assay. Environ. Toxicol. Chem. 19, 2154-2165.

Scotcher, M. C., and Bennett, G. N. (2005) SpoIIE regulates sporulation but does not directly affect solventogenesis in Clostridium acetobutylicum ATCC824. J. Bacteriol. 187, 1930-1936.

Spain, J. C. (1995) Biodegradation of nitroaromatic compounds. Annual Review of Microbiology 49, 634-649.

Lee, S.Y.; Mermelstein, L. D.; Bennett, G.N.; Papoutsakis, E.T.; (1992) Vector Construction, Transformation, and Gene Amplification in Clostridium acetobutylicum ATCC 824. Annals NY Academy of Sciences, 39-51.

Rao, G., and Mutharasan, R. (1987) Altered electron flow in continuous cultures of Clostridium acetobutylicum induced by viologen dyes. Appl. Environ. Microbiol. 53, 1232-1235.

Wang, J., Zhu, J., Bennett, G. N., and San, K. Y. (2011) Succinate production from different carbon sources under anaerobic conditions by metabolic engineered *Escherichia coil* strains. Metabolic engineering 13, 328-335.

Shin, C. Y., and Crawford, D. L. (1995) Biodegradation of trinitrotoluene (TNT) by a strain of Clostridium bifermentans. In Bioaugmentation for Site Remediation (Hinchee, R. W., Fredrickson, J., and Alleman, B. C., eds), Battelle Press, Columbus.

Ahmad, F., and Hughes, J. B. (2000) Anaerobic Transformation of TNT by Clostridium. In Biodegradation of Nitroaromatic Compounds and Explosives (Spain, J. C., Hughes, J. B., and Knackmuss, H.-J., eds) pp. 185-212, Lewis Publishers/CRC Press, Boca Raton.

* cited by examiner

| Compound | $E°$ |
|---|---|
| Methylene blue | 0.011 |
| Brilliant alizarine blue | -0.040 |
| PCA | -0.116 |
| Indigo-disulfonate | -0.125 |
| 2-Hydroxy-1,4-naphthoquinone | -0.137 to -0.145 |
| 2-Amino-1,4-naphthoquinone | -0.133 to -0.137 |
| Gallophenine | -0.142 |
| Anthraquinone 1,5-disulfonate | -0.170 to -0.175 |
| Anthraquinone 2,6-disulfonate | -0.184 |
| Anthraquinone 2-sulfonate | -0.225 |
| Phenosafranine | -0.252 to 0.255 |
| TNT | -.253 |
| Neutral Red | -0.325 |
| Methyl Violgen | -0.430 |
| Methyl Red | -0.395 |

Table 3. Metabolites of C. acetobutylicum cultures before and during TNT degradation.

The table compares the glucose consumption as it relates cultures before TNT addition and in the hour following TNT addition. The table compares the glucose consumption as it relates to acid formation and reducing equivalents in the cultures before TNT addition and in the hour following TNT addition. Measured ethanol levels were very low (~0.2 mM) and did not change by more than 0.05 mM, acetone levels were also very low (~0.05 mM) and did not change by more than 0.04 mM, no butanol was measured in any of the samples.

| Strain | acetate (mM) | Butyrate (mM) | Acetate-butyrate ratio | glucose used (mM)[a] | NADH glycol[b] | NAD+ acid formed[c] | Net NADH[d] | Fdred PFOR[e] | Net available reducing eq[f] | Net NADH used per glucose | $CO_2$ (mM) Formed[g] | Red Eq available for H2 formation per $CO_2$[h] |
|---|---|---|---|---|---|---|---|---|---|---|---|---|
| 824 Prior | 3.76 | 4.31 | 0.87 | 6.19 | 12.38 | 8.62 | 3.76 | 12.38 | 16.14 | 0.61 | 12.38 | 1.30 |
| 824 During | 1.63 | 5.8 | 0.28 | 6.615 | 13.23 | 11.6 | 1.63 | 13.23 | 14.86 | 0.25 | 13.23 | 1.12 |
| M5 Prior | 3.71 | 4.32 | 0.86 | 6.175 | 12.35 | 8.64 | 3.71 | 12.35 | 16.06 | 0.60 | 12.35 | 1.30 |
| M5 During | 0.82 | 7.05 | 0.12 | 7.46 | 14.92 | 14.1 | 0.82 | 14.92 | 15.74 | 0.11 | 14.92 | 1.05 |

Figure 3:
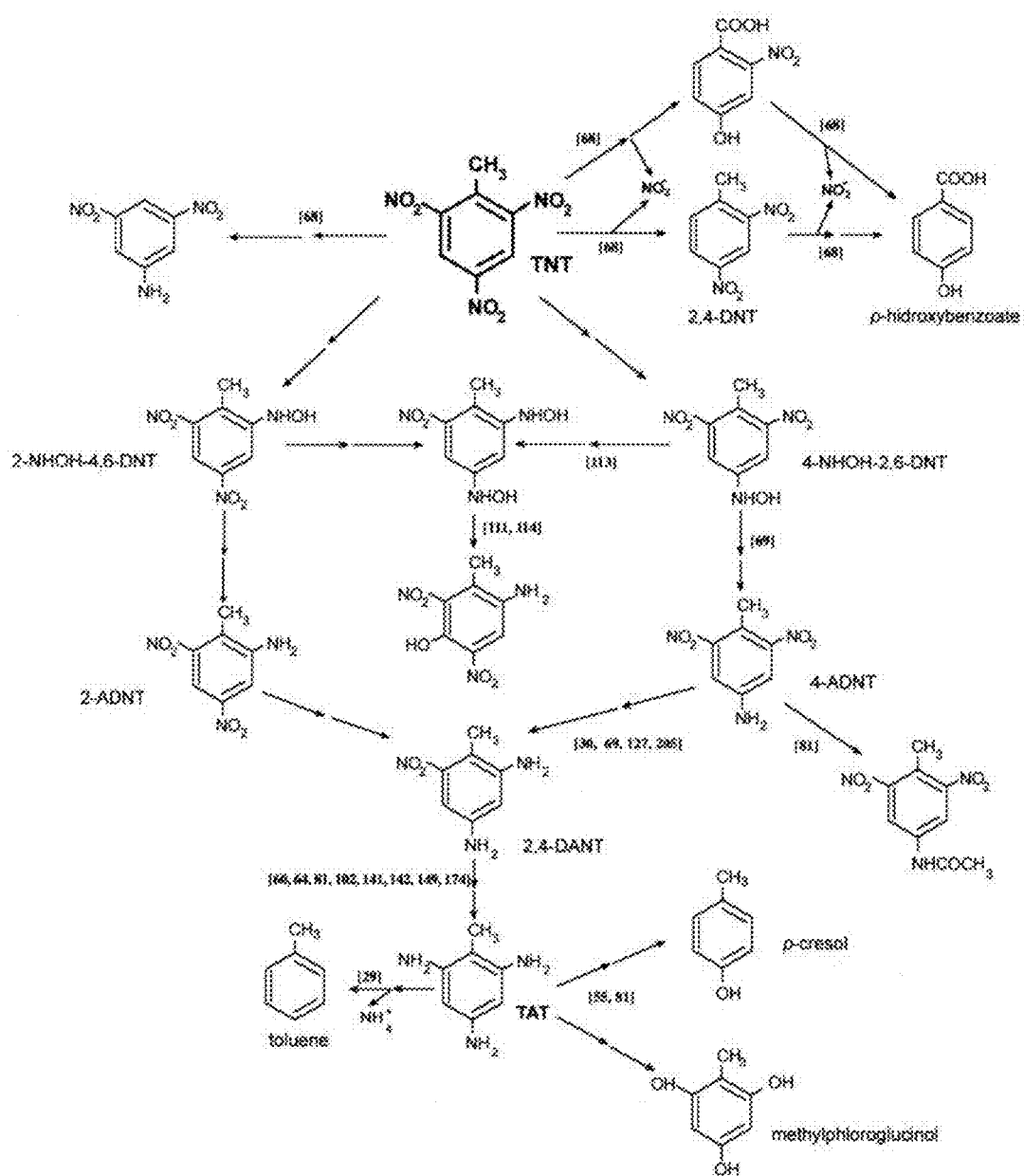

[a] Glucose consumed is based upon acetate and butyrate.
[b] NADH glycolysis assumes two NADHs per glucose.
[c] The NAD+ acid formation is the calculated amount of reduction equivalent consumed in producing the acids, acetate and butyrate.
[d] The net NADH is calculated as the total NADH available from glycolysis minus the amount used in formation of the acids.
[e] The reduced ferredoxin formed through conversion of pyruvate to acetyl-CoA by pyruvate ferredoxin oxidoreductase considering two reduced ferredoxins per glucose consumed.
[f] The net available reducing equivalents is the amount of net NADH available plus the reduced ferredoxin.
[g] The $CO_2$ formed per glucose is two times the glucose consumed.
[h] The redox equivalent available for hydrogen production per $CO_2$ is calculated as the net available reducing equivalents (see footnote f) divided by the CO2 produced (see footnote g). This value correlates well with the experimental values measured in Figure 3, value before TNT addition of ~1.36 and the period after of ~1.18.

FIG. 8

LONG CHAIN ORGANIC ACID BIOPRODUCTION

This application is a National Phase filing under 35 U.S.C. §371 of International Application PCT/US2012/071038, filed on Dec. 20, 2012, which claims priority to U.S. Ser. No. 61/579,480, filed Dec. 22, 2011. Both applications are expressly incorporated herein by reference in their entirety.

FEDERALLY SPONSORED RESEARCH STATEMENT

This invention was made with government support under Grant No: W911NF-09-1-0119 awarded by the Army Research Office. The government has certain rights in the invention.

REFERENCE TO MICROFICHE APPENDIX

Not applicable.

BACKGROUND OF THE INVENTION

Trinitrotoluene ("TNT") is a common nitroaromatic compound contaminating the surface and subsurface soil of many military sites. This yellow-colored solid is sometimes used as a reagent in chemical synthesis, but it is best known as a useful explosive material with convenient handling properties.

TNT is poisonous, and skin contact can cause skin irritation, causing the skin to turn a bright yellow-orange color. During the First World War, munition workers who handled the chemical found that their skin turned bright yellow, which resulted in their acquiring the nickname "canary girls" or simply "canaries." Consumption of TNT produces red urine through the presence of breakdown products and not blood as sometimes believed. Anemia, abnormal liver functions, spleen enlargement and other harmful effects on the immune system have also been found in animals that ingested or breathed trinitrotoluene. There is evidence that TNT adversely affects male fertility and it is listed as a possible human carcinogen. Thus, the toxicity and mutagenicity of TNT has been widely known for decades.

Typically, TNT contamination has been treated by incineration. However, due to the high cost of incineration treatments and the toxicity of incineration products, other methods of decontamination are needed. Bioremediation has become a promising and cost-effective decontamination measure. Indeed, a variety of aerobic and anaerobic bacteria, and even fungi and plants can degrade TNT. When compared to incineration, the previously most common method of biodegradation, bioremediation is both less expensive and less environmentally hazardous.

Figures 6, 7:
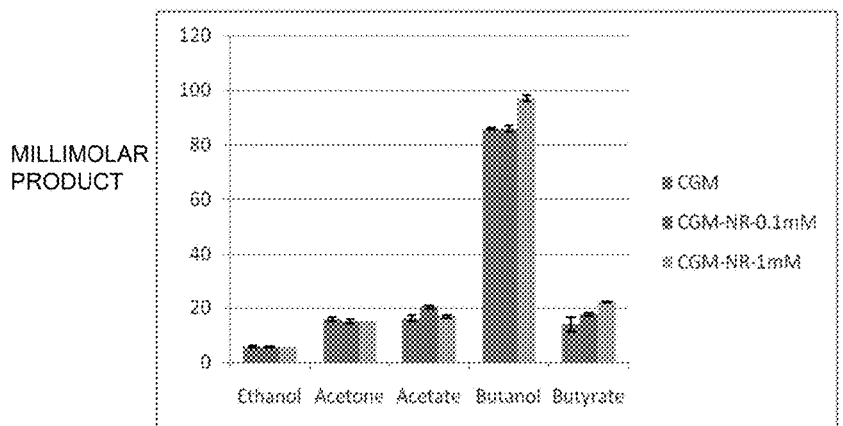

Bioremediation of TNT by some aerobic microorganisms is problematic, however, because many common degradation pathways lead to the formation of toxic and mutagenic degradation intermediates. TNT consists of a benzene ring, a methyl group, and three nitro groups. When degradation occurs by reducing these nitro groups in a step-wise fashion, the aromatic ring is left uncleaved. These degradation intermediates have been shown to be toxic and/or mutanagenic. Anaerobic degradation pathways, in contrast, avoid these toxic intermediates. Proposed mechanisms for anaerobic TNT metabolism in bacteria are shown in FIG. 6.

The Clostridia are an example of obligate anaerobes that can degrade TNT. *C. acetobutylicum* is known to enzymatically reduce TNT primarily through the activity of an iron-only hydrogenase, which transfers electrons to TNT through an iron-sulfur center. Related microorganisms reported to anoxically degrade or transform TNT are listed below:

| Microorganism | Metabolism |
| --- | --- |
| *Clostridium acetobutylicum* | Reduction of TNT to TAT |
| *Clostridium bifermentans* CYS-1 | Degrades TNT to aliphatic polar compounds via 4ADNT and 2,4DANT |
| *Clostridium bifermentans* LJP-1 | Transforms TNT into TAT and phenolic compounds |
| *Clostridium pasterianum* | Reduction of TNT to TAT |
| *Clostridium sordelii* | Reduction of TNT to TAT |
| *Clostridium* sp. | Bamberger rearrangement of dihydroxyl-aminonitrotoluene |
| *Desulfovibrio* sp. strain B | TNT as nitrogen source, toluene as a putative intermediate |
| *Desulfovibrio* sp. | TNT as the sole nitrogen source; reduction of TNT to TAT |
| *Desulfovibrio* sp. | Transforms TNT into TAT and DANT; 42% of radioactivity from [$^{14}$C]TNT is associated with cell biomass |
| *Escherichia coli* | Reduction of TNT to TAT |
| *Lactobacillus* sp. | Reduction of TNT to TAT |
| *Methanococcus* sp. strain B | Reduction of TNT to DANT |
| *Pseudomonas* sp. strain JLR11 | TNT as nitrogen source; TNT as final electron acceptor |
| *Veillonella alkalescens* | Reduction of TNT to TAT |

While studying the degradation of TNT by *Clostridium acetobutylicum*, an important goal in and of itself, we serendipitously discovered a general method that can be used to drive the production of longer carbon feedstock chemicals in anaerobes having an iron-based hydrogenase. Such methods have value in the art because longer chain molecules can be made into a wider variety of chemicals and because many organisms preferentially produce metabolites having fewer carbons.

SUMMARY OF THE INVENTION

The invention relates to the fields of anaerobic microbial culture techniques to produce feedstock and other chemicals.

In particular, addition of an electron carrier of the appropriate redox potential to the culture can enhance the production of the longer chain length acids. This is important in industrial efforts to make medium chain organic acids. While many bacteria make acetic acid as a major product, the longer chain length acids, such as butyric acid, hexanoic acid, and others that are feedstocks of four or more carbons, are more undustrially valuable.

We performed the exemplary experiments in *Clostridium*. However, it is predicted that any anaerobe that has a Fe based hydrogenase should work and the redistribution to whatever reduced product is available can be made depending on if its substrate is available to the cell to act as a sink for the reducing power. We predict that most soil anaerobes will function in the invention, as long as they have a hydrogenase that receives its input from ferredoxin, like the FeFe hydrogenase of *Clostridium*.

We exemplified the concept using the redox compounds TNT and PCA, as well as dyes outside the efficacious range, but FIG. 7 includes a variety of redox dyes, within the window of −0.253 to −0.116 V based on midpoint potential from the standard hydrogen electrode at pH 7.

The invention is adding a redox active compound with a redox potential of between −0.116 to −0.253 V to a culture capable of forming hydrogen via a hydrogenase so that the redox potential is diverted from hydrogen to form a longer chain acid. One redox active compound with a redox potential of −0.253 V is trinitrotoluene and its use as an example is shown below, another redox active compound is phenazine-1 carboxylic acid with a redox potential of −0.116 V. The action of other redox molecules outside this range, such as methylene blue and methyl viologen, do not show the same effect on butyrate versus acetate production.

Method of producing organic acids having at least 4 carbons in Clostridial cells are provided, comprising growing Clostridial cells in a medium supplemented by the addition of a redox compound with a redox potential −0.116 to −0.253 volts; growing said Clostridial cells, and isolating organic acids having at least 4 carbons.

The redox compound can be added to a concentration of 10-100 µM, although the amount is expected to vary with the redox compound being chosen, and the cell type employed, some redox compounds having more toxicity than others.

A variety of organisms can be used in the invention, including those anaerobes having an ferrodoxin based hydrogenase. Examplary microbes include *Clostridium acetobutylicum, C. bifermentans* CYS-1, *C. bifermentans* LIP-1, *C. pasterianum, C. sordelii*, C. sp., *Desulfovibrio* sp. strain B, *Desulfovibrio* sp., *Methanococcus* sp. strain B, *Pseudomonas* sp. strain ARIL *Veillonella alkalescens, C. tyrobutyricum, C. kluyveri*, and acetogenic *Clostridium.*

We also predict it would work on engineered organisms which have had the Fd system added to their normal metabolic capacity, such as may be done in *E. coli, Lactobacillus, Lactococcus, Bacillus*, or *Corynebacterium*. For example, the ferrodoxin hydrogenase from *Clostridum* (hydA, e.g., AAB03723 and maturation genes hydEF and hydG) could be added to *E. coli*, and competing pathways (e.g., adhE) shut off or downregulated. See e.g., King 2006.

Any suitable culture medium can be used, and sugars, minerals, proteins extracts, antibiotics, and the like can be added to said cultures.

The effect is observed best during the exponential phase of during anaerobic growth, at least in the obligate anaerobes studied herein. However, the effect may be observable in other organisms when the competing pathways (e.g., adhE) are turned off.

In preferred embodiments, the redox compound is trinitrotoluene ("TNT") or phenazine-1 carboxylic acid ("PCA"), but the redox compound can be any compound selected from those listed in FIG. 7, or any compound having a redox potential −0.116 to −0.253 V at the conditions used.

In some embodiments, the organic acid produced is butyrate, but any C3 or higher, or C4 or higher, organic acids made by the microbe in question can be produced, e.g., hexanoic acid.

Method of producing butyrate are also provided, comprising growing Clostridial cells in a medium supplemented by the addition of about 50 μM of phenazine-1 carboxylic acid; growing said Clostridial cells, and isolating said butyrate.

As used herein, the acid and salt forms are used interchangably, thus butyrate and butyric acid are used interchangeably.

The following abbreviations are used herein:

| Abbreviation | Name |
|---|---|
| TNT | Trinitrotoluene |
| PCA | phenazine-1 carboxylic acid |

-continued

| Abbreviation | Name |
|---|---|
| Fd | Ferrodoxin |
| hydA | Gene encoding H(2)-evolving hydrogenase |
| hydE | Gene encoding Iron-only hydrogenase maturase |
| hydF | Gene encoding Iron-only hydrogenase maturase |
| pSOS | Plasmid encoding the egenes needed for butanol production |
| as | Antisense |
| OD | Optical Density, see also $A_{600}$ which is the absorbance at 600 nm |
| − | Refers to a disrupted gene. |
| + | Refers to an overexpressed gene |
| CGM | Clostridial growth medium |
| MB | Methylene blue |
| NR | Neutral red |

DESCRIPTION OF FIGURES

FIG. 1 Comparison of TNT degradation rates among *C. acetobutylicum* strains with different genetic backgrounds (different solvent profiles) revealed no major differences. The rate of TNT transformation was assayed during the early exponential phase ($A_{600}$ 0.3), mid-exponential phase ($A_{600}$ 1.0) and stationary phase (24 hour culture with $A_{600}$ varied) by diluting the culture at different times into fresh medium containing 400 μM TNT. Standard deviations are shown.

FIG. 2 Diagram of redox cofactor utilization upon TNT addition. The NADH made during glycolysis is channeled to formation of butyrate when the ferredoxin to hydrogenase reaction is altered by the presence of TNT.

FIG. 3 proposed mechanism for anaerobic TNT metabolism. The schema is taken from Abraham Esteve-Núñez, et al., Biological Degradation of 2,4,6-Trinitrotoluene, Microbiol Mol Biol Rev. 2001 September; 65(3): 335-352. When the conversion of a compound to another is believed to occur through a series of intermediates, the steps are indicated by two arrows.

FIG. 4 Cultures were grown with CGM medium plus the indicated amounts of PCA for 50 hours, and showing the concentration of the indicated metabolites. A variety of cultures of *C. acetobutylicum* were tested, and all showed similar results. Cultures where the pH was buffered were also examined. Shown here is wild type *C. acetobutylicum*

FIG. 5 Wild type *C. acetobutylicum* were grown with CGM medium plus the indicated amounts of Methylene Blue (MB) for 50 hours and showing the concentration of the indicated metabolites.

FIG. 6 Wild type *C. acetobutylicum* were grown with CGM medium plus the indicated amounts of neutral red (NR) for 50 hours and showing the concentration of the indicated metabolites.

FIG. 7 Redox potential of various dyes for use in the invention.

FIG. 8. Metabolites of *C. acetobutylicum* cultures before and during TNT degradation.

DESCRIPTION OF THE INVENTION

We studied TNT degradation by Clostridia, as part of our efforts to develop suitable bioremediation treatments for contaminated sites. However, as a result of the metabolic studies underlying our bioremediation work, we also found that TNT addition to cell culture can affect the metabolite profile of such organisms.

Experiments designed to elucidate the underlying mechanism for this phenomena showed that during TNT degradation, the cells shift metabolism away from hydrogen formation towards reduction of TNT, and the resulting effects on cell redox cofactors generate a higher proportion of butyrate than would otherwise occur as part of the cells effort to reduce excess. Furthermore, these results were fairly consistent across a variety of cell genetic backgounds tested, although only a selection of data is presented herein. It is our hypothesis, that the cells eliminate the excess NADH in the only way they can—by making acetoacetyl coA, and thus bypassing the acetylCo, that leads to acetate. Thus, the cells accumulate more butyrate than acetate.

We then tested a number of colored molecules with a range of redox potentials, and found that those molecules with a range of redox potential −0.116 to −0.253 V show similar effects, while dyes outside this range do not. Thus, the method has generally applicability in driving Clostridia and other ferrodoxin hydrogenase containing anaerobes towards the production of butyrate and other C4 and higher products.

Materials:

2,4,6-trinitrotoluene, 2,6-dinitrotoluene, 2-amino-4,6-dinitrotoluene and 4-amino-2,6-dinitrotoluene were purchased from ChemService (Westchester, Pa., USA); p-nitrotoluene and 2,4-dinitrotoluene were purchased from Sigma-Aldrich (St. Louis, Mo., USA); 2-hydroxylamino-4,6-dinitrotoluene, 4-hydroxylamino-2,6-dinitrotoluene and 2,4-diamino-6-nitrotoluene were from SRI International (Menlo Park, Calif., USA).

All medium components for *Clostridium* culture were obtained from Difco (Detroit, Mich., USA) or Sigma-Aldrich (St. Louis, Mo., USA). All Restriction enzymes were obtained from New England Biolabs, Inc. (Beverly, Mass., USA). pCR2.1-TOPO vector from Invitrogen Corporation (Carlsbad, Calif., USA) was used for PCR product cloning. Automated DNA sequencing was performed by LoneStar automated DNA sequencing (LoneStar Laboratories Inc., Houston, Tex.).

Bacterial Strains, Plasmids and Growth Conditions:

All bacteria strains and plasmids are listed in Table 1.

TABLE 1

Bacterial strains and plasmids

| Strain/Plasmid | Description[a] | Reference/source[b] |
|---|---|---|
| Strains | | |
| *Clostridium acetobutylicum* | | |
| ATCC 824 | Wild type | ATCC |
| M5 | pSOL1 | (Clark et al. 1989) |
| 824(buk−) | Disruption of butyrate kinase gene in 824 | (Green et al. 1996) |
| 824(pta−) | Disruption of phosphotrans-acetylase gene in 824 | (Green et al. 1996) |
| 824(Mutant B) | Disruption of SolR by pO1X | (Nair et al. 1999) |
| *Escherichia coli* | | |
| DH10β | mcrA ΔmcrBC recA1 Str[r] | NEB |
| Plasmids | | |
| pSOS 94 | ptb promoter, Ap[r] MLS[r] ColE I, repL | (Tummala et al. 2003) |
| pSC12 | Thl[r], shuttle vector, ColE I, repL | (Zhao et al. 2003) |
| pDHKM | Km[r], Φ3TI methyltransferase in pDHK29 | (Zhao et al. 2003) |
| pSOS-del | Control plasmid based on pSOS94 by deletion of *clostridium* structural genes | This study |
| pSOS-as-hydA | Antisense down-regulation of hydA gene | This study |
| pSOS-as-hydE | Antisense down-regulation of hydE gene | This study |
| pSOS-as-hydF | Antisense down-regulation of hydF gene | This study |
| pSOS-hydA | Overexpression of hydA gene | This study |

[a]mcrA ΔmcrBC, methylcytosine-specific restriction system abolished; recA1, homologous recombination abolished; Str[r], streptomycin resistant; MLS[r], macrolide-lincosamide-streptogramin B resistant; repL, plM13 gram-positive origin of replication; ColE I, gram-negative origin of replication; Km[r], kanamycin resistant; Ap[r], ampicillin resistant; Str[r], streptomycin resistant; Thl[r], thiamphenicol resistant.
[b]ATCC, American Type Culture Collection, Manassas, VA.; NEB, New England Biolabs, Beverly, Mass.

*E. coli* cultures were grown aerobically at 37° C. in Luria-Bertani (LB) medium, *C. acetobutylicum* was grown anaerobically at 37° C. in buffered *Clostridium* growth medium (CGM) in a Form a Scientific anaerobic chamber (Thermo Form a, Marietta, Ohio) as described previously (Cai and Bennett 2011; Zhao et al. 2005). For *E. coli* recombinant strains, the medium was supplemented with ampicillin (100 µg/mL), chloramphenicol (35 µg/mL), kanamycin (50 µg/ml), or erythromycin (200 µg/mL) as appropriate.

For *C. acetobutylicum* strains, erythromycin (40 µg/mL for solidified agar plate and 100 µg/mL for liquid medium) and thiamphenicol (25 µg/mL) were used when necessary. For long-term storage, *E. coli* strains were cultivated and stored as glycerol stocks at −80° C. *C. acetobutylicum* strains were stored as lyophilized stocks at room temperature or glycerol stocks at −80° C. (Scotcher and Bennett 2005).

Analysis of Fermentation Products:

Cell growth was monitored by $A_{600}$ with a Beckman DU-800 spectrophotometer. On fermentor, cell growth was monitored by a cell density sensor. The concentrations of butanol, acetone, ethanol, butyrate, and acetate were determined using gas chromatography with a Hewlett-Packard 5890 Series II instrument (Hewlett-Packard Company, Palo Alto, Calif.) as described previously (Scotcher and Bennett 2005; Zhao et al. 2003; Zhao et al. 2005). Glucose was measured by HPLC as described (Wang et al. 2011).

TNT Assay in *C. acetobutylicum* Culture:

TNT concentration in the culture medium was followed by a spectrometric protocol modified from Jenkins et al (Jenkins and Walsh 1992; Watrous et al. 2003). Freshly made sodium sulfite solution (0.2 g/mL) in 50 mM pH 8.0 Tris-HCl buffer reacts with TNT solution to form a colored complex with maximum absorption at $A_{414}$ that remains stable for hours under assay conditions. $A_{414}$ readings increase linearly up to a 500 µM TNT concentration.

Single *C. acetobutylicum* colonies from freshly grown plates were inoculated into buffered CGM medium with appropriate antibiotics and incubated overnight as seed cultures. An appropriate amount from seed culture was used for the subculture to yield a starting $A_{600}$ of 0.1. The culture was incubated at 37° C. and growth ($A_{600}$) measured periodically. TNT degradation rate was assayed during early-exponential phase ($A_{600}$ 0.3), mid-exponential phase ($A_{600}$ 1.0) and stationary phase (24 hour culture with $A_{600}$ varied) by diluting the culture at different times into fresh medium containing 400 µM TNT. At different time points, 250 µL samples were taken and immediately reacted with 750 µL sodium sulfite solution by vortex; the samples were further centrifuged at 14000 rpm for 10 minutes and the supernatant was used for the TNT spectrophotometric assay. The TNT degradation rate $\mu_{max}$ for different strains were compared by calculating the rate of TNT decrease during the first 40 minutes.

In order to determine the effect of culture dilution on TNT degradation and confirm the linear range of the measurements, five C. acetobutylicum cultures were prepared to ultimately yield 10×, 20×, 30×, 40×, and 50× dilutions respectively. For each dilution sample, three subcultures were made. The appropriate amounts of C. acetobutylicum ($A_{600}$ 0.3) and CGM/TNT mixture, for a total volume of 10 mL, were transferred anaerobically into 15 mL culture tubes. The tubes were immediately vortexed, and a 0.25 mL sample of each tube was added to 0.75 mL assay buffer. The tubes were left to incubate at 37° C., and 0.25 mL samples were again taken at 20 minutes and 40 minutes. All operations were conducted in the anaerobic chamber, and all solutions were pre-equilibrated in the chamber for twenty-four hours. Once the three time samples were collected and centrifuged at 13000 rpm for 10 minutes, the $A_{414}$ absorbance of each supernatant was measured, and the dilution factors were considered to calculate the specific TNT degradation rates. Since the time of the initial rate measurement was short after the dilution compared to a typical lag phase recovery of growth rate the measured rates are considered indicative of the metabolism of the cell at the time points used.

The Colorimetric TNT Assay Protocol:

A simplified Jenkins TNT assay protocol was adapted in our experiments. Major nitro-compounds and TNT metabolites do not interfere with our TNT assay, in which TNT showed an absorption peak at 414 nm, while other partially reduced species did not. The other nitro compounds showed absorption peaks around 350 nm with a much lower intensity than the peak at 414 nm for TNT (data not shown). The measured TNT concentration in the culture declined with time during the assay, and the rate of decrease had diminished considerably after 1 hr.

It was found that sample dilution affected the calculated specific TNT degradation rate. Samples of Clostridial cultures diluted in higher volumes of the CGM/TNT mixture exhibited increasing levels of specific TNT degradation rate up to a dilution factor of 40, and further dilution incurred no additional effect on the specific rate of transformation. Therefore the maximal specific TNT degradation rate as measured by this method was used in the figures and tables.

TNT Degradation Rate is Relatively Stable:

Strains of C. acetobutylicum were compared for their rate of TNT degradation. The strains analyzed were the wild type ATCC 824; strain M5 (Clark et al. 1989; Stim-Herndon et al. 1996), a strain that has lost the pSOL plasmid and does not produce butanol; strain 824(pta⁻), with a disrupted phosphotransacetylase gene, pta, which produces a lower level of acetate during the early phase of culture; strain, 824(buk⁻) with a disrupted butyrate kinase gene, buk, which produces butyrate at a lower level during the early phase of culture (Green et al. 1996); and 824 (Mutant B) a strain that has a disruption in the gene upstream of the solvent operon and has increased butanol formation (Nair et al. 1999).

These strains could reveal differences in the TNT transformation rate correlated with the metabolite pattern of the cells, especially in the early log phase. Since the metabolic mutations affected the products of early metabolism and this change in metabolic pattern could in turn affect the relative proportion of hydrogen produced during the early log phase. For example, the difference in acetate versus butyrate production can result in a different level of hydrogen formation and potentially alter the availability of reductant for TNT transformation. Also since some of these strains, the buk⁻ and mutant H and mutant B strains, have been shown previously to enter the solvent producing phase earlier than the wild type parent, it was anticipated they may have lower ability to transform TNT in the early or mid log phase samples as they would be physiologically more like the early solvent producing state.

Samples from cultures of each C. acetobutylicum strain (Table 1) were diluted in order to measure the initial rate of the TNT transformation of the specific culture. To measure the TNT degradation rate during different growth phases samples were analyzed from cultures at $A_{600}$ 0.3 (for early exponential phase), $A_{600}$ 1.0 (for mid-exponential phase) and 24-hour culture (for stationary phase culture, solventgenic phase).

The initial rate of TNT degradation in each culture is shown in FIG. 1. The experiment shows the maximal rate of the reaction with different strains and cell preparations. It was found that all strains tested showed similar initial TNT degradation rate, ranging from 10,000-12,000 µM/Hour/$A_{600}$ during the early exponential phase. All strains tested showed the same trend of a decrease in the specific TNT degradation rate with the advancement of growth phase, with those entering or in the stationary-solvent producing phase having the lowest specific rate of TNT transformation.

The maximal specific TNT degradation rate may be limited by hydrogenase levels or by other factors such as the glucose uptake rate, growth rate, supply of reductant ($Fd_{reduced}$) or other components. To investigate the effects of these other factors, analyses were done on the medium before and during the time the TNT was being degraded.

In order to quantitate the glucose metabolism during the TNT transformation, the metabolites were analyzed from parental C. acetobutylicum ATCC824 cultures degrading TNT at the high rates presented in FIG. 1. Since the amount of glucose utilization during the period of TNT degradation was low, we assessed the metabolism during this period by two independent measurements. We measured glucose directly and also measured the metabolic products of glucose metabolism (acetate and butyrate) independently. The TNT degradation rate measured in this series of five culture experiments gave a TNT degradation rate of 15.2 mM/h/ A600.

Glucose uptake rates in three of the culture experiments were found by measurement of the acetate and butyrate concentrations before and after the TNT degradation period. The correlation to glucose utilization used the stoichiometric amount of acetate and butyrate produced by Clostridia cultures ($A_{600}$=0.3) within an hour of TNT addition. Since the stoichiometric ratio of metabolites produced to glucose consumed is 2:1 for acetate and 1:1 for butyrate, the molar increase observed in these two products during the first hour was used to determine the amount of glucose metabolism to acids during the period of TNT transformation. Ethanol and butanol were measured and discounted from the analysis as negligible. These measurements gave glucose uptake rates of 22, 26 and 34 mM/Hour/$A_{600}$.

In two of the experiments, the glucose uptake by Clostridia culture ($A_{600}$=0.3) was analyzed by HPLC directly. For each experiment, the glucose concentration values were measured both before and after the hour-long run with TNT. The rate of glucose consumption was directly determined from the concentration difference showing values of 17 and 14 mM/h/$A_{600}$. The ratios of TNT to glucose metabolism in these TNT studies ranged from 0.45 to 1.0. So it appeared, a mole of TNT was reduced for about every 1-2 moles of metabolized glucose.

These relatively high ratios suggest that TNT can be reduced competitively against regular cellular metabolism and that when operating at the maximal rate, TNT reduction is not a minor factor in the cells metabolic activities and can represent a significant distortion and sink for the cell's reducing power. Thus, rather than being a minor side reaction of the cells metabolism, the TNT is an effective in vivo reactant with the redox carriers/enzymes such as reduced ferredoxin-hydrogenase, and it can affect the cells metabolism during this time.

The reaction with TNT not only can use a significant proportion of the cells reducing power, but in doing this it affects the overall pattern of metabolism and is in turn affected by competitors which influence the redox situation, e.g. the more effective diversion of redox to solvent producing redox pathways later in the culture. This perspective would place TNT among the group of dyes that can be reduced by *Clostridium* (Rao and Mutharasan 1987), and thus this work could have broader implications in the general control/understanding of redox regulation and response in these anaerobes.

In the case of TNT, the reduction is irreversible and continues beyond an initial reduction step (Hughes et al. 1998a; Hughes et al. 1998b), while for many dyes the reaction is reversible and the reduced dye can transfer electrons to another carrier or redox reaction and affect the metabolite pattern.

We found TNT addition alters the redox potential of the culture. Addition of TNT to cultures in exponential growth resulted in a dose dependent spike in the redox potential (not shown). This initial spike was followed by a persistent increase in the redox potential of the cultures receiving TNT when compared to the redox level of the control culture. The relative increase in redox potential lasted for the remainder of exponential growth, indicating that TNT addition results in a change to the culture's redox status for three hours.

We also observed addition of TNT resulted in a decrease of hydrogen production by cultures of *C. acetobutylicum* ATCC 824. TNT can act as an alternative electron acceptor for the hydrogenase enzyme, so the effect of TNT addition on $H_2$ production in cultures during exponential growth was determined by measuring the $H_2/CO_2$ ratio. The data (not shown) shows that there was a sharp reduction in the $H_2/CO_2$ ratio following the addition of TNT, which was due to a decrease in $H_2$ production since $CO_2$ production remained relatively constant. This provides further evidence that TNT can compete with the natural electron acceptors of the hydrogenase enzyme in actively growing cells and indicates that TNT reduction could alter the metabolic output of the cells.

We also noted that when TNT was added, and the reaction proceeded over a period of time, a different metabolic pattern was seen—more butyrate and less acetate were observed in a variety of Clostridia cultures studied.

We measured the acid metabolites formed during the time after TNT addition. A culture of *C. acetobutylicum* grown under the conditions where the TNT degradation rate was analyzed was processed and subjected to gas chromatography to determine the metabolites present in the pre-TNT added culture and in the culture 1 hour after the TNT addition, a time when the starting TNT had been depleted. The culture continued to grow during this time and the metabolism of glucose continued during the 1 hour period and seemed unchanged in rate as judged by the total production of acids during this time. However, analysis of the metabolites formed over the period during TNT transformation showed a significant change in the proportions of acetate and butyrate, with a large amount of butyrate being produced in comparison to very little acetate (Table 3).

In the study presented in FIG. 1, the results show only a small reduction in the TNT degradation rate in the $pta^-$, $buk^-$ and mutant H or B strains during the medium log phase. It was anticipated that the different metabolite patterns might affect the availability of reductant for hydrogen formation and thus affect TNT degradation by the reductant going into the hydrogenase reaction. The small effect in the mid-log phase may have been due to more reductant going to butyrate in the $pta^-$ mutant since this strain is known to form more butyrate early in the culture (Green et al. 1996) so there could be less available for hydrogenase mediated TNT reduction in this phase of the culture. In the buk and mutant H or B strain studies, a small reduction of the rate of TNT transformation was observed in the mid-log phase and this small effect could be due to an earlier transition to the more stationary, solvent phase physiological state where the cell has low ability to transform TNT (Green et al. 1996; Khan et al. 1997).

If one considers the total reductant available and that some of the redox goes to reduce the TNT, initially it might seem that the loss of this reducing power would lessen the amount of butyrate formed, since formation of butyrate from pyruvate requires more reduction than formation of acetate. However if we examine the process of reduction to form hydrogen and butyrate we see a difference in cofactor used. In the formation of hydrogen, the cofactor is reduced ferredoxin generated by the pyruvate:ferredoxin oxidoreductase in the conversion of pyruvate to acetyl-CoA, providing one reduced Fd per pyruvate consumed and for each $CO_2$ released, and this is supplemented to some degree by conversion of some of the NADH formed in glycolysis via a NADH-ferredoxin reductase.

In the early growth stage we are studying there is no formation of the reduced solvents, ethanol and butanol and the enzymes forming these compounds are not induced under this growth condition. The normal ratio of acetate to butyrate 1:1 then gives a value of 1.3-1.4 for the $H_2/CO_2$ ratio and a use of more Fd than would be generated by the pyruvate:ferredoxin reductase indicating use of some NADH to form reduced Fd for the extra hydrogen formation (Table 3). In this circumstance, the shift to more butyrate formation during the period of TNT reduction by the ferredoxin-Fe hydrogenase in our anaerobic chamber experiments, can be considered as a result of a difference in the cofactor balance.

With TNT it appeared that blockage of the usual hydrogenase acceptance of reductant from reduced ferredoxin was lessened, and thus the NADH-ferredoxin reductase reaction did not proceed as well as normal. This situation then resulted in more NADH being available in the cell and since the NADH must be recycled, it was consumed by conversion of acetyl-CoA to butyrate.

The cell cannot reduce acetyl-CoA directly due to a lack of aldehyde-alcohol dehydrogenase (e.g. AdhE), because alcohol forming genes and proteins are not expressed during this early growth phase. Thus, there are few options available to recycle the NADH, and it appeared the NADH was recycled to NAD+ through conversion of the acetyl-CoA to acetoacetyl-CoA, beta-hydroxylbutyryl-CoA, crotonyl-CoA and butyryl-CoA. This route was already operating to a good extent in the cell since almost equivalent molar amounts of acetate and butyrate were formed during the normal acid phase culture and the normal proportion of acids yielded a hydrogen to carbon dioxide ratio of approximately 1.3-1.4 in the pre TNT culture (not shown) and which is consistent with previous literature where uncontrolled pH batch early phase cultures were studied (Husemann and Papoutsakis 1990; Zhao et al. 2003).

Figure 2:
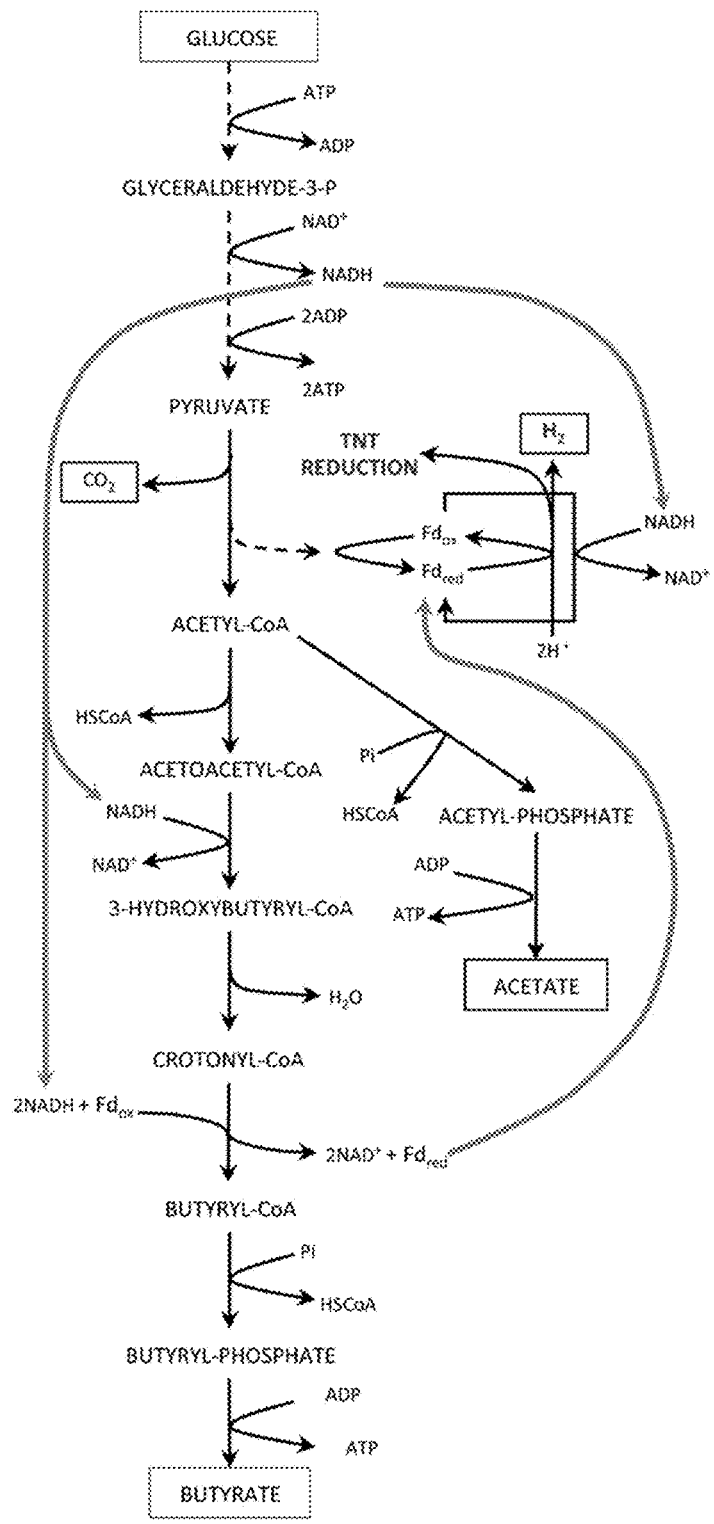

The pathway for acetyl-CoA to butyryl-CoA allowed consumption of 2 NADH per molecule of butyrate formed and relieved the cofactor imbalance between ferredoxin and NADH since NADH is the reductant used in this pathway. The redistribution observed also points to the relative ability of TNT to both be reduced by hydrogenase and inhibit the reaction of hydrogenase by serving as an alternative to ferredoxin. In this way the addition of TNT effectively removes a portion of the normal role of hydrogenase while it acts as a competing substrate and leads to a build-up and redistribution of the substrate for the hydrogenase (i.e. reduced ferredoxin) as shown in FIG. 2.

The detailed redox calculations shown in Table 3 analyzes the redistribution of reductant from production of hydrogen to more production of butyrate during the time when TNT was present and being reduced. The level of TNT present (400 μM) would not consume much of the reductant available directly in this experiment, and the amount would be expected to be 1 mM or less based on the early reduction steps of TNT under these conditions as analyzed previously (Ahmad and Hughes 2000; Khan et al. 1997; Padda et al. 2000).

Calculations of the observed reductant consumed in the formation of acids either before or during TNT transformation and the resulting reducing equivalents available for formation of hydrogen give values of 1.30 for the hydrogen/$CO_2$ ratio before TNT addition and 1.05-1.12 during TNT degradation. These values are very close to the values measured experimentally (not shown), before TNT addition of 1.36 and during TNT degradation of 1.18.

If the data are presented in a form where the fraction of total reductant formed from glucose metabolism, i.e. reduced ferredoxin and NADH, that goes to either formation of hydrogen or butyrate is calculated, we can analyze the proportion of reductant that is consumed in butyrate formation in the culture during the one hour period before TNT addition and it is 35% of the total reductant. If the same calculation is done on the culture during the one hour period of TNT degradation a proportion of 44-47% of total reductant that goes into formation of butyrate is determined.

The variation of hydrogenase activity observed fits with the finding of Watrous et al. (Watrous 2003) and was shown in our other work, not presented here, that hydA antisense lowered the expression and activity of hydrogenase and TNT reduction activity. On the other hand, increasing the amount of hydrogenase through overexpression affected the rate of TNT transformation in cells to only a small degree, less than two fold, while the expression of the hydA gene as determined by Rt-PCR was elevated by ~50 fold. These results suggest the limitation on reducing capacity seems to be at least partially due to the availability of reduced ferredoxin to transfer reducing equivalents to hydrogenase or TNT.

The results also fits with the observation shown in FIG. 1, in which the TNT reducing activity is lower in cultures in the solventogenic phase, at a time when there is more diversion of electrons from ferredoxin to NAD+. This situation is apparently due to increased activity of the ferredoxin-NADH reductase, which is capable of lowering the amount of reduced ferredoxin available for interaction with hydrogenase. Additionally, the lower amount of hydrogenase activity found in such cultures means that the capacity of the cells to transfer electrons from hydrogen or reduced Fd to TNT is reduced. The results of previous studies on the ferredoxins of *C. acetobutylicum* and the level of the NADH-ferredoxin reductase and the ferredoxin-NAD reductase in cells grown under different conditions are consistent with this explanation (Girbal and Soucaille 1994; Vasconcelos et al. 1994).

These findings of the effect of competition of other factors and intracellular cofactor pathways on TNT reduction pave the way for more detailed investigation of the effects these parameters play in defining the rate of TNT degradation in the natural environment. This is particularly interesting in light of the analysis of natural mobile soluble electron carriers in native soil ecosystems where molecules such as quinones, phenazines, and humic acids exist or are made and released by a variety of soil organisms.

The presence of these compounds that could act as competitors or inhibitors of reduced ferredoxin reactions with hydrogenase and TNT could also influence the availability of reduced ferredoxin and allow the shuttling of reductant to other pathways in the cell, e.g. those using NADH and limiting the availability of reduced ferredoxin. This feature would mimic the situation in the later phase cultures where a lower rate of TNT degradation is observed.

Thus, to define the "real world" effectiveness of various microbial communities to degrade TNT, not only do we need to consider the major groups of direct degraders such as Clostridia and their substrates (sugars, and polymeric substrates such as cellulose) in the environment that enable growth but we also need to consider the community population and small redox molecules in the soil which may generate e-carrier competitors to the reaction with TNT and cell redox processes. The presence of these other natural electron carriers may play a role in limiting the performance of Clostridial TNT degradation in contaminated sites.

The above studies showed the amount of TNT degraded contributed a substantial proportion of the metabolic redox available during the consumption of glucose during the culture. Table 4 shows the that a considerable of the cells available redox can go to TNT reduction under optimal conditions and that the reaction studied can be a major contributor to total redox partitioning. This shows it is not just a minor side reaction unconnected to main metabolism.

TABLE 4

| | Exp. 1 | Exp. 2 | Exp. 3 | Exp. 4 | Exp. 5 | Exp. 6 | Exp. 7 |
| --- | --- | --- | --- | --- | --- | --- | --- |
| TNT deg. Rate (mM/Hour/$A_{600}$) | 15.2 | 15.2 | 15.2 | 15.2 | 15.2 | 2.0 | 2.0 |
| Glucose uptake rate (mM/Hour/$A_{600}$) | 22.0 | 26.2 | 33.9 | 16.9 | 14.3 | 4.7 | 3.9 |
| TNT rate/ Glucose rate | 0.691 | 0.580 | 0.448 | 0.899 | 1.06 | 0.43 | 0.51 |

Glucose uptake rates for experiments 1-3 were found by analyzing the amount of acetate and butyrate produced by Clostridia cultures (A=0.3) within an hour of TNT addition. Since the stoichiometric ratio of solvent produced to glucose consumed is 2:1 for acetate and 1:1 for butyrate, the molar increase observed in these two products during the first hour was used to estimate glucose metabolism. Other solvents produced were discounted as negligible.

Experiments 4-5 were a pair of identical TNT assays where the glucose uptake by Clostridia culture (A=0.3) was analyzed by HPLC. For each experiment, the glucose concentration values were measured both before and after the hour-long run with TNT. The rate of glucose consumption was directly determined from the concentration difference.

Experiments 6-7 were taken from outside literature and were conducted in the absence of TNT. Information from profiles of glucose uptake by *C. acetobutylicum* cultures (A=1.0) was extrapolated to estimate the consumption rate in the conditions used in our own experiments. The ratios of TNT to glucose metabolism in our TNT assays ranged from 0.448 to 1.06, which is comparable to the range extrapolated from the other papers' data, 0.43-0.51. In all of the experiments, a mole of TNT was reduced for about every 1-2 moles of metabolized glucose. These relatively high ratios confirm that TNT can be reduced competitively against regular cellular metabolism.

Analysis of the metabolites formed over the period when TNT is being transformed (Table 5) shows a significant change in the proportions of acetate and butyrate.

TABLE 5

Metabolites of *C. acetobutylicum* cultures before and after TNT addition

| Strain | Ethanol mM | Acetone mM | Acetate mM | Butanol mM | Butyrate mM |
|---|---|---|---|---|---|
| *C. acetobutylicum* 824 pre TNT | 0.23 | 0.07 | 3.76 | 0 | 4.31 |
| *C. acetobutylicum* 824 1 hr post TNT | 0.29 | 0.03 | 5.39 | 0 | 10.11 |
| *C. acetobutylicum* 824 during TNT | 0.06 | 0 | 1.63 | 0 | 5.8 |
| *C. acetobutylicum* M5 pre TNT | 0.10 | 0.02 | 3.71 | 0 | 4.32 |
| *C. acetobutylicum* M5 1 hr post TNT | 0 | 0 | 4.53 | 0 | 11.37 |
| *C. acetobutylicum* M5 during TNT | 0 | 0 | 0.82 | 0 | 7.05 |

The above results show that TNT in the culture broth significantly increased the amount of butyrate formed in a wide variety of genetic backgrounds. This suggested to us that electron carriers could be used to affect the profile of metabolites produced in culture, driving production towards e.g., longer acids.

In order to investigate the role of other electron carriers we examined a variety of electron carrier dyes with different redox potentials on the pattern of metabolites of the *Clostridium acetobutylicum* cultures. The effects of various redox dyes on the pattern of acids was studied, and the results shown in FIG. 4-6.

Figure 4:
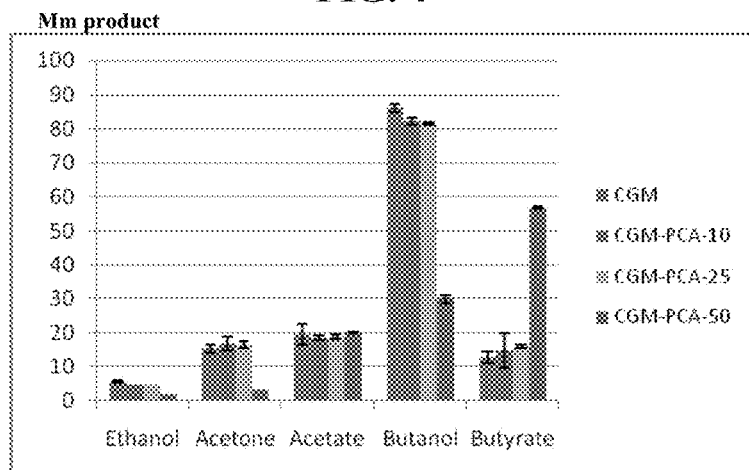
Figure 5:
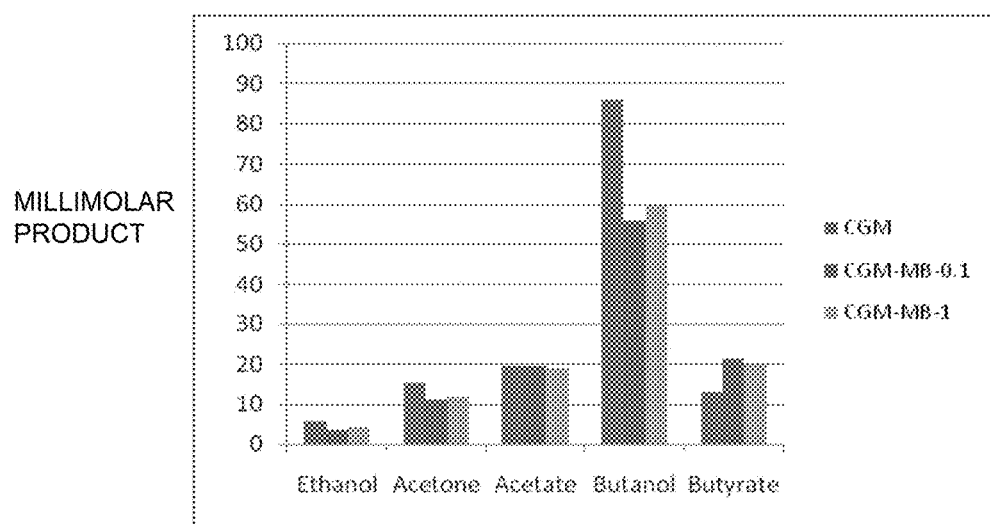

With 50 uM phenazine-1-carboxylic acid (PCA) (redox potential −0.113) cultures showed a much higher ratio of butyrate to acetate in FIG. 4. By contrast, dyes with redox potential outside a range do not change metabolite profiles. See FIG. 5-6.

These results show that addition of a redox compound with the redox potential −0.116 to −0.253 V produces more longer chain organic acid molecules and fewer short chain organic acid molecules, and thus can be used in cultures of same to improve production levels. Redox compounds outside this range lack the effect. The redox potential and effect of various dyes is summarized in FIG. 7, where the shaded area represents useful molecules.

All references cited herein are incorporated by reference in their entireties for all purposes.

1. Ahmad, F., and Hughes, J. B. (2000) Anaerobic Transformation of TNT by *Clostridium*. In *Biodegradation of Nitroaromatic Compounds and Explosives* (Spain, J. C., Hughes, J. B., and Knackmuss, H.-J., eds) pp. 185-212, Lewis Publishers/CRC Press, Boca Raton.
2. Spain, J. C. (1995) Biodegradation of nitroaromatic compounds. *Annual Review of Microbiology* 49, 634-649.
3. Won, W. D., Salvo, L. H. d., and Ng, J. (1976) Toxicity and mutagenicity of 2,4,6-trinitrotoluene and its microbial metabolites. *Appl. Environ. Microbiol.* 31, 576-580.
4. Siciliano, S. D., Gong, P., Sunahara, G. I., and Greer, C. W. (2000) Assessment of 2,4,6-trinitrotoluene toxicity in field soils by pollution-induced community tolerance, denaturing gel electrophoresis, and seed germination assay. *Environ. Toxicol. Chem.* 19, 2154-2165.
5. Padda, R. S., Wang, C. Y., Hughes, J. B., and Bennett, G. N. (2000) Mutagenicity of trinitrotoluene and its metabolites formed during anaerobic degradation by *Clostridium acetobutylicum* ATCC 824. *Environ. Toxicol. Chem.* 19, 2871-2875.
6. Tan, E. L., Ho, C. H., Griest, W. H., and Tyndall, R. L. (1992) Mutagenicity of trinitrotoluene and its metabolites formed during composting. *J. Toxicol. Environ. Health* 36, 165-172.
7. Shin, C. Y., and Crawford, D. L. (1995) Biodegradation of trinitrotoluene (TNT) by a strain of *Clostridium bifermentans*. In *Bioaugmentation for Site Remediation* (Hinchee, R. W., Fredrickson, J., and Alleman, B. C., eds), Battelle Press, Columbus.
8. Daun, G., Lenke, H., Reuss, M., and Knackmuss, H. J. (1998) Biological treatment of TNT-contaminated soil. 1. Anaerobic cometabolic reduction and interaction of TNT and metabolites with soil components. *Environ. Sci. Technol.* 32, 1956-1963.
9. Frische, T., and Hoper, H. (2003) Soil microbial parameters and luminescent bacteria assays as indicators for in situ bioremediation of TNT-contaminated soils. *Chemosphere* 50, 415-427.
10. Eyers, L., Smoot, J. C., Smoot, L. M., Bugli, C., Urakawa, H., McMurry, Z., Siripong, S., El-Fantroussi, S., Lambert, P., Agathos, S, N., and Stahl, D. A. (2006) Discrimination of shifts in a soil microbial community associated with TNT-contamination using a functional ANOVA of 16S rRNA hybridized to oligonucleotide microarrays. *Environmental science & technology* 40, 5867-5873.
11. Wu, Y., Luo, Y., Zou, D., Ni, J., Liu, W., Teng, Y., and Li, Z. (2008) Bioremediation of polycyclic aromatic hydrocarbons contaminated soil with *Monilinia* sp.: degradation and microbial community analysis. *Biodegradation* 19, 247-257.
12. Watrous, M. M., Clark, S., Kutty, R., Huang, S., Rudolph, F. B., Hughes, J. B., and Bennett, G. N. (2003) 2,4,6-trinitrotoluene reduction by an Fe-only hydrogenase in *Clostridium acetobutylicum*. *Appl Environ Microbiol* 69, 1542-1547.
13. Kutty, R., and Bennett, G. N. (2006) Studies on inhibition of transformation of 2,4,6-trinitrotoluene catalyzed by Fe-only hydrogenase from *Clostridium acetobutylicum*. *J Ind Microbiol Biotechnol* 33, 368-376.
14. Cai, X., and Bennett, G. N. (2011) Improving the *Clostridium acetobutylicum* butanol fermentation by engineering the strain for co-production of riboflavin. *Journal of industrial microbiology & biotechnology* 38, 1013-1025.

15. Zhao, Y., Tomas, C. A., Rudolph, F. B., Papoutsakis, E. T., and Bennett, G. N. (2005) Intracellular butyryl phosphate and acetyl phosphate concentrations in *Clostridium acetobutylicum* and their implications for solvent formation. *Appl Environ Microbiol* 71, 530-537.

16. Scotcher, M. C., and Bennett, G. N. (2005) SpoIIE regulates sporulation but does not directly affect solventogenesis in *Clostridium acetobutylicum* ATCC824. *J. Bacteriol.* 187, 1930-1936.

17. Zhao, Y., Hindorff, L. A., Chuang, A., Monroe-Augustus, M., Lyristis, M., Harrison, M. L., Rudolph, F. B., and Bennett, G. N. (2003) Expression of a cloned cyclopropane fatty acid synthase gene reduces solvent formation in *Clostridium acetobutylicum* ATCC 824. *Appl Environ Microbiol* 69, 2831-2841.

18. Wang, J., Zhu, J., Bennett, G. N., and San, K. Y. (2011) Succinate production from different carbon sources under anaerobic conditions by metabolic engineered *Escherichia coli* strains. *Metabolic engineering* 13, 328-335.

19. Girbal, L., and Soucaille, P. (1994) Regulation of *Clostridium acetobutylicum* metabolism as revealed by mixed-substrate steady-state continuous cultures: role of NADH/NAD ratio and ATP pool. *J Bacteriol* 176, 6433-6438.

20. Vasconcelos, I., Girbal, L., and Soucaille, P. (1994) Regulation of carbon and electron flow in *Clostridium acetobutylicum* grown in chemostat culture at neutral pH on mixtures of glucose and glycerol. *J Bacteriol* 176, 1443-1450.

21. van der Zee, F. P., Bouwman, R. H., Strik, D. P., Letting a, G., and Field, J. A. (2001) Application of redox mediators to accelerate the transformation of reactive azo dyes in anaerobic bioreactors. *Biotechnology and bioengineering* 75, 691-701.

22. Hongo, M. (1957) Butanol fermentation part X. Increase in the reduction of C4-system by neutral red. *Nippon Nogeikagaka Kaishi* 31, 731-735.

23. Aristidou, A. A., San, K. Y., and Bennett, G. N. (1999) Improvement of biomass yield and recombinant gene expression in *Escherichia coli* by using fructose as the primary carbon source. *Biotechnology progress* 15, 140-145.

24. Rao, G., and Mutharasan, R. (1987) Altered electron flow in continuous cultures of *Clostridium acetobutylicum* induced by viologen dyes. *Appl. Environ. Microbiol.* 53, 1232-1235.

25. Peguin, S., and Soucaille, P. (1996) Modulation of metabolism of *Clostridium acetobutylicum* grown in chemostat culture in a three-electrode potentiostatic system with methyl viologen as electron carrier. *Biotechnology and bioengineering* 51, 342-348.

26. Peguin, S., and Soucaille, P. (1995) Modulation of Carbon and Electron Flow in *Clostridium acetobutylicum* by Iron Limitation and Methyl Viologen Addition. *Applied and environmental microbiology* 61, 403-405.

27. King, P. W., et al., Functional Studies of [FeFe] Hydrogenase Maturation in an *Escherichia coli* Biosynthetic System, J. Bacteriol. (2006) 188(6), 2163-2172.

We claim:

1. A method of producing increased amounts of butyric acid, said method comprising culturing a *Clostridium* cell in a medium including sugar and a redox compound with a standard redox potential −0.116 to −0.253 V without using external electrodes to change the redox potential in the medium until said butyric acid is produced, wherein the redox compound is phenazine-1 carboxylic acid ("PCA") present at about 50 µM; and wherein the amount of the produced butyric acid is increased by at least 30% as compared to without supplementation of the redox compound.

2. The method of claim 1, wherein said *Clostridium* cells are selected from a group consisting of *Clostridium acetobutylicum, Clostridium bifermentans, Clostridium pasterianum, Clostridium sordelii, Clostridium* sp., *Clostridium tyrobutyricum*, and *Clostridium kluyveri*.

3. The method of claim 1, further comprising adding sugars to said media.

* * * * *